(12) United States Patent
Quisenberry

(10) Patent No.: US 9,950,148 B2
(45) Date of Patent: *Apr. 24, 2018

(54) WOUND CARE METHOD AND SYSTEM WITH ONE OR BOTH OF VACUUM-LIGHT THERAPY AND THERMALLY AUGMENTED OXYGENATION

(71) Applicant: ThermoTek, Inc., Flower Mound, TX (US)

(72) Inventor: Tony Quisenberry, Highland Village, TX (US)

(73) Assignee: ThermoTek, Inc., Flower Mound, TX (US)

( * ) Notice: Subject to any disclaimer, the term of this patent is extended or adjusted under 35 U.S.C. 154(b) by 579 days.

This patent is subject to a terminal disclaimer.

(21) Appl. No.: 14/062,428

(22) Filed: Oct. 24, 2013

(65) Prior Publication Data
US 2014/0052054 A1 Feb. 20, 2014

Related U.S. Application Data

(63) Continuation of application No. 13/359,210, filed on Jan. 26, 2012, now Pat. No. 8,632,576, which is a
(Continued)

(51) Int. Cl.
*A61N 5/06* (2006.01)
*A61N 5/00* (2006.01)
(Continued)

(52) U.S. Cl.
CPC ............... *A61M 37/00* (2013.01); *A61F 7/02* (2013.01); *A61M 35/00* (2013.01); *A61N 5/00* (2013.01);
(Continued)

(58) Field of Classification Search
CPC ........ A61N 5/062; A61N 5/00; A61N 5/0624; A61N 2005/0645; A61N 2005/0649;
(Continued)

(56) References Cited

U.S. PATENT DOCUMENTS 773,828 A 11/1904 Titus
2,110,022 A 3/1938 Kliesrath
(Continued)

FOREIGN PATENT DOCUMENTS

CH 670 541 6/1989
DE 35 22 127 1/1987
(Continued)

OTHER PUBLICATIONS

U.S. Appl. No. 14/197,324, Quisenberry.
(Continued)

*Primary Examiner* — Gary Jackson
*Assistant Examiner* — Boniface N Nganga
(74) *Attorney, Agent, or Firm* — Winstead PC

(57) ABSTRACT

A system for treatment of a wound area of a patient including a first treatment pad comprising a plurality of Light Emitting Diodes (LEDs) for cleaning and exposing a wound area to ultraviolet light, a second treatment pad comprising removal ports for exposing the wound area to a negative pressure, and a control unit interoperably connected to the first and second treatment pads for providing a negative pressure and the ultraviolet light to the wound area.

10 Claims, 11 Drawing Sheets

Related U.S. Application Data continuation-in-part of application No. 11/975,047, filed on Oct. 17, 2007, now Pat. No. 8,128,672, which is a continuation-in-part of application No. 11/801,662, filed on May 9, 2007, now Pat. No. 8,100,956.

(60) Provisional application No. 61/479,156, filed on Apr. 26, 2011, provisional application No. 60/798,982, filed on May 9, 2006, provisional application No. 60/852,803, filed on Oct. 19, 2006.

(51) Int. Cl.

| | | |
|---|---|---|
| A61M 37/00 | (2006.01) | |
| A61F 7/02 | (2006.01) | |
| A61M 35/00 | (2006.01) | |
| A61F 7/00 | (2006.01) | |
| A61H 33/14 | (2006.01) | |

(52) U.S. Cl.
CPC .... *A61N 5/0624* (2013.01); *A61F 2007/0054* (2013.01); *A61F 2007/0295* (2013.01); *A61F 2007/0296* (2013.01); *A61H 33/14* (2013.01); *A61N 2005/0645* (2013.01); *A61N 2005/0649* (2013.01); *A61N 2005/0652* (2013.01); *A61N 2005/0661* (2013.01)

(58) Field of Classification Search
CPC ... A61N 2005/0652; A61N 2005/0661; A61M 37/00; A61M 35/00; A61F 2007/0054; A61F 2007/0295; A61F 2007/0296; A61F 7/02; A61H 33/14
USPC .......................................... 607/88–89; 606/9
See application file for complete search history.

(56) References Cited

U.S. PATENT DOCUMENTS

| | | |
|---|---|---|
| 2,504,308 A | 4/1950 | Donkle, Jr. |
| 3,014,117 A | 12/1961 | Madding |
| 3,164,152 A | 1/1965 | Vere Nicoll |
| 3,179,106 A | 4/1965 | Meredith |
| 3,345,641 A | 10/1967 | Jennings |
| 3,367,319 A | 2/1968 | Carter, Jr. |
| 3,548,809 A | 12/1970 | Conti Francesco |
| 3,608,091 A | 9/1971 | Olson et al. |
| 3,660,849 A | 5/1972 | Jonnes et al. |
| 3,736,764 A | 6/1973 | Chambers et al. |
| 3,738,702 A | 6/1973 | Jacobs |
| 3,744,053 A | 7/1973 | Parker et al. |
| 3,744,555 A | 7/1973 | Fletcher et al. |
| 3,862,629 A | 1/1975 | Rotta |
| 3,894,213 A | 7/1975 | Agarwala |
| 4,006,604 A | 2/1977 | Seff |
| 4,013,069 A | 3/1977 | Hasty |
| 4,029,087 A | 6/1977 | Dye et al. |
| 4,206,751 A | 6/1980 | Schneider |
| 4,224,941 A | 9/1980 | Stivala |
| 4,375,217 A | 3/1983 | Arkans |
| 4,402,312 A | 9/1983 | Villari et al. |
| 4,459,468 A | 7/1984 | Bailey |
| 4,459,822 A | 7/1984 | Pasternack |
| 4,471,787 A | 9/1984 | Bentall |
| 4,503,484 A | 3/1985 | Moxon |
| 4,523,594 A | 6/1985 | Kuznetz |
| 4,547,906 A | 10/1985 | Nishida et al. |
| 4,590,925 A | 5/1986 | Dillon |
| 4,597,384 A | 7/1986 | Whitney |
| 4,608,041 A | 8/1986 | Nielsen |
| D285,821 S | 9/1986 | Kneisley |
| D288,372 S | 2/1987 | Adams |
| 4,660,388 A | 4/1987 | Greene, Jr. |
| 4,738,249 A | 4/1988 | Linman et al. |
| D295,897 S | 5/1988 | Thimm-Kelly |
| 4,741,338 A | 5/1988 | Miyamae |
| 4,795,435 A | 1/1989 | Steer |
| 4,821,354 A | 4/1989 | Little |
| 4,844,072 A | 7/1989 | French et al. |
| 4,884,304 A | 12/1989 | Elkins |
| 4,901,200 A | 2/1990 | Mazura |
| 4,911,231 A | 3/1990 | Horne et al. |
| 4,926,881 A | 5/1990 | Ichinomiya et al. |
| 4,962,761 A | 10/1990 | Golden |
| 4,969,881 A | 11/1990 | Viesturs |
| 4,979,375 A | 12/1990 | Nathans et al. |
| 4,989,589 A | 2/1991 | Pekanmaki et al. |
| 4,995,698 A | 2/1991 | Myers |
| 4,996,970 A | 3/1991 | Legare |
| 5,044,364 A | 9/1991 | Crowther |
| 5,051,562 A | 9/1991 | Bailey et al. |
| D320,872 S | 10/1991 | McCrane |
| 5,062,414 A | 11/1991 | Grim |
| 5,067,040 A | 11/1991 | Fallik |
| 5,080,089 A | 1/1992 | Mason et al. |
| 5,090,409 A | 2/1992 | Genis |
| 5,092,271 A | 3/1992 | Kleinsasser |
| 5,097,829 A | 3/1992 | Quisenberry |
| 5,106,373 A | 4/1992 | Augustine et al. |
| 5,112,045 A | 5/1992 | Mason et al. |
| 5,117,812 A | 6/1992 | McWhorter |
| 5,125,238 A | 6/1992 | Ragan et al. |
| 5,165,127 A | 11/1992 | Nicholson |
| 5,179,941 A | 1/1993 | Siemssen et al. |
| 5,184,612 A | 2/1993 | Augustine |
| 5,186,698 A | 2/1993 | Mason et al. |
| 5,230,335 A | 7/1993 | Johnson, Jr. et al. |
| 5,232,020 A | 8/1993 | Mason et al. |
| 5,241,951 A | 9/1993 | Mason et al. |
| 5,243,706 A | 9/1993 | Frim et al. |
| 5,263,538 A | 11/1993 | Amidieu et al. |
| 5,285,347 A | 2/1994 | Fox et al. |
| D345,082 S | 3/1994 | Wenzl |
| D345,609 S | 3/1994 | Mason et al. |
| D345,802 S | 4/1994 | Mason et al. |
| D345,803 S | 4/1994 | Mason et al. |
| 5,300,101 A | 4/1994 | Augustine et al. |
| 5,300,102 A | 4/1994 | Augustine et al. |
| 5,300,103 A | 4/1994 | Stempel et al. |
| 5,303,716 A | 4/1994 | Mason et al. |
| 5,315,994 A * | 5/1994 | Guibert .................... A61F 7/00 607/101 |
| 5,316,250 A | 5/1994 | Mason et al. |
| D348,106 S | 6/1994 | Mason et al. |
| 5,323,847 A | 6/1994 | Koizumi et al. |
| 5,324,319 A | 6/1994 | Mason et al. |
| 5,324,320 A | 6/1994 | Augustine et al. |
| D348,518 S | 7/1994 | Mason et al. |
| 5,330,519 A | 7/1994 | Mason et al. |
| 5,336,250 A | 8/1994 | Augustine |
| 5,343,579 A | 9/1994 | Dickerhoff et al. |
| 5,350,417 A | 9/1994 | Augustine |
| D351,472 S | 10/1994 | Mason et al. |
| 5,352,174 A | 10/1994 | Mason et al. |
| 5,354,117 A | 10/1994 | Danielson et al. |
| D352,781 S | 11/1994 | Mason et al. |
| 5,360,439 A | 11/1994 | Dickerhoff et al. |
| 5,370,178 A | 12/1994 | Agonafer et al. |
| 5,371,665 A | 12/1994 | Quisenberry et al. |
| D354,138 S | 1/1995 | Kelly |
| D357,747 S | 4/1995 | Kelly |
| 5,402,542 A | 4/1995 | Viard |
| 5,405,370 A | 4/1995 | Irani |
| 5,405,371 A | 4/1995 | Augustine et al. |
| 5,407,421 A | 4/1995 | Goldsmith |
| D358,216 S | 5/1995 | Dye |
| 5,411,494 A | 5/1995 | Rodriguez |
| 5,411,541 A | 5/1995 | Bell et al. |
| 5,417,720 A | 5/1995 | Mason |
| 5,440,450 A | 8/1995 | Lau et al. |
| 5,449,379 A | 9/1995 | Hadtke |
| 5,466,250 A | 11/1995 | Johnson, Jr. et al. |
| 5,496,262 A | 3/1996 | Johnson, Jr. et al. |
| 5,496,357 A | 3/1996 | Jensen et al. |

(56) References Cited

U.S. PATENT DOCUMENTS

| | | |
|---|---|---|
| 5,505,726 A | 4/1996 | Meserol |
| 5,507,792 A | 4/1996 | Mason |
| 5,509,894 A | 4/1996 | Mason et al. |
| 5,514,079 A | 5/1996 | Dillon |
| 5,528,485 A | 6/1996 | Devilbiss et al. |
| 5,561,981 A | 10/1996 | Quisenberry et al. |
| 5,566,062 A | 10/1996 | Quisenberry et al. |
| D376,013 S | 11/1996 | Sandman et al. |
| 5,578,022 A | 11/1996 | Scherson et al. |
| 5,588,954 A | 12/1996 | Ribando et al. |
| 5,591,200 A | 1/1997 | Cone et al. |
| 5,636,643 A | 6/1997 | Argenta et al. |
| D380,874 S | 7/1997 | Caswell |
| 5,645,081 A | 7/1997 | Argenta et al. |
| 5,648,716 A | 7/1997 | Devilbiss et al. |
| D383,546 S | 9/1997 | Amis et al. |
| D383,547 S | 9/1997 | Mason et al. |
| D383,848 S | 9/1997 | Mason et al. |
| 5,662,695 A | 9/1997 | Mason et al. |
| 5,669,872 A | 9/1997 | Fox |
| 5,672,152 A | 9/1997 | Mason et al. |
| 5,675,473 A | 10/1997 | McDunn et al. |
| 5,682,748 A | 11/1997 | DeVilbiss et al. |
| 5,689,957 A | 11/1997 | DeVilbiss et al. |
| 5,690,849 A | 11/1997 | DeVilbiss et al. |
| 5,711,029 A | 1/1998 | Visco et al. |
| 5,711,155 A | 1/1998 | DeVilbiss et al. |
| D393,073 S | 3/1998 | Downing et al. |
| 5,731,954 A | 3/1998 | Cheon |
| 5,733,321 A | 3/1998 | Brink |
| D394,707 S | 5/1998 | Tsubooka |
| 5,755,755 A | 5/1998 | Panyard |
| 5,772,618 A | 6/1998 | Mason et al. |
| 5,782,780 A | 7/1998 | Mason et al. |
| 5,795,312 A | 8/1998 | Dye |
| 5,807,294 A | 9/1998 | Cawley et al. |
| 5,827,208 A | 10/1998 | Mason |
| 5,831,824 A | 11/1998 | McDunn et al. |
| D403,779 S | 1/1999 | Davis et al. |
| D404,490 S | 1/1999 | Tripolsky |
| D405,884 S | 2/1999 | Roper |
| 5,865,841 A | 2/1999 | Kolen et al. |
| 5,871,526 A | 2/1999 | Gibbs et al. |
| 5,890,371 A | 4/1999 | Rajasubramanian et al. |
| 5,901,037 A | 5/1999 | Hamilton et al. |
| 5,923,533 A | 7/1999 | Olson |
| 5,947,914 A | 9/1999 | Augustine |
| 5,980,561 A | 11/1999 | Kolen et al. |
| 5,989,285 A | 11/1999 | DeVilbiss et al. |
| 6,007,559 A | 12/1999 | Arkans |
| 6,055,157 A | 4/2000 | Bartilson |
| 6,058,010 A | 5/2000 | Schmidt et al. |
| 6,058,712 A | 5/2000 | Rajasubramanian et al. |
| 6,080,120 A | 6/2000 | Sandman et al. |
| D428,153 S | 7/2000 | Davis |
| D430,288 S | 8/2000 | Mason et al. |
| D430,289 S | 8/2000 | Mason et al. |
| 6,117,164 A | 9/2000 | Gildersleeve et al. |
| 6,125,036 A | 9/2000 | Kang et al. |
| 6,129,688 A | 10/2000 | Arkans |
| 6,135,116 A | 10/2000 | Vogel et al. |
| 6,156,059 A | 12/2000 | Olofsson |
| 6,176,869 B1 | 1/2001 | Mason et al. |
| 6,186,977 B1 | 2/2001 | Andrews et al. |
| 6,231,532 B1 | 5/2001 | Watson et al. |
| 6,235,049 B1 | 5/2001 | Nazerian |
| 6,238,427 B1 | 5/2001 | Matta |
| 6,260,890 B1 | 7/2001 | Mason |
| 6,270,481 B1 | 8/2001 | Mason et al. |
| 6,295,819 B1 | 10/2001 | Mathiprakasam et al. |
| 6,305,180 B1 | 10/2001 | Miller et al. |
| 6,319,114 B1 | 11/2001 | Nair et al. |
| 6,352,550 B1 | 3/2002 | Gildersleeve et al. |
| 6,358,219 B1 | 3/2002 | Arkans |
| 6,368,592 B1 | 4/2002 | Colton et al. |
| 6,436,064 B1 | 8/2002 | Kloecker |
| 6,443,978 B1 | 9/2002 | Zharov |
| 6,462,949 B1 | 10/2002 | Parish, IV et al. |
| 6,468,237 B1 | 10/2002 | Lina |
| 6,508,831 B1 | 1/2003 | Kushnir |
| D472,322 S | 3/2003 | Hoglund et al. |
| D473,315 S | 4/2003 | Miros et al. |
| D473,656 S | 4/2003 | Miros et al. |
| D473,948 S | 4/2003 | Elkins et al. |
| 6,551,264 B1 | 4/2003 | Cawley et al. |
| 6,551,347 B1 | 4/2003 | Elkins |
| D474,544 S | 5/2003 | Hoglund et al. |
| 6,562,060 B1 | 5/2003 | Momtaheni |
| 6,596,016 B1 | 7/2003 | Vreman |
| 6,648,904 B2 | 11/2003 | Altshuler et al. |
| D484,601 S | 12/2003 | Griffiths et al. |
| D484,602 S | 12/2003 | Griffiths et al. |
| 6,660,027 B2 | 12/2003 | Gruszecki et al. |
| 6,667,883 B1 | 12/2003 | Solis et al. |
| 6,675,072 B1 | 1/2004 | Kerem |
| D486,870 S | 2/2004 | Mason |
| 6,695,823 B1 | 2/2004 | Lina et al. |
| 6,719,713 B2 | 4/2004 | Mason |
| 6,719,728 B2 | 4/2004 | Mason et al. |
| 6,736,787 B1 | 5/2004 | McEwen et al. |
| D492,411 S | 6/2004 | Bierman |
| 6,775,137 B2 | 8/2004 | Chu et al. |
| D496,108 S | 9/2004 | Machin et al. |
| 6,789,024 B1 | 9/2004 | Kochan, Jr. et al. |
| 6,802,823 B2 | 10/2004 | Mason |
| D499,846 S | 12/2004 | Cesko |
| 6,834,712 B2 | 12/2004 | Parish et al. |
| 6,846,295 B1 | 1/2005 | Ben-Nun |
| 6,848,498 B2 | 2/2005 | Seki et al. |
| 6,855,158 B2 | 2/2005 | Stolpmann |
| 6,893,414 B2 | 5/2005 | Goble et al. |
| D506,553 S | 6/2005 | Tesluk |
| 6,935,409 B1 | 8/2005 | Parish, IV et al. |
| 6,936,019 B2 | 8/2005 | Mason |
| D510,140 S | 9/2005 | Brown |
| 6,945,988 B1 | 9/2005 | Jones |
| D510,626 S | 10/2005 | Krahner et al. |
| D515,218 S | 2/2006 | McGuire et al. |
| 7,004,915 B2 | 2/2006 | Boynton et al. |
| D523,147 S | 6/2006 | Tesluk |
| 7,066,949 B2 | 6/2006 | Gammons et al. |
| 7,081,128 B2 | 7/2006 | Hart et al. |
| D533,668 S | 12/2006 | Brown |
| 7,198,046 B1 | 4/2007 | Argenta et al. |
| 7,216,651 B2 | 5/2007 | Argenta et al. |
| D551,351 S | 9/2007 | Silva |
| D551,352 S | 9/2007 | Frangi |
| 7,306,568 B2 | 12/2007 | Diana |
| 7,354,411 B2 | 4/2008 | Perry et al. |
| D568,482 S | 5/2008 | Gramza et al. |
| D569,985 S | 5/2008 | Ganapathy et al. |
| 7,427,153 B1 | 9/2008 | Jacobs et al. |
| 7,429,252 B2 | 9/2008 | Sarangapani |
| 7,484,552 B2 | 2/2009 | Pfahnl |
| 7,492,252 B2 | 2/2009 | Maruyama |
| 7,524,286 B2 | 4/2009 | Johnson |
| 7,532,953 B2 | 5/2009 | Vogel |
| 7,553,306 B1 | 6/2009 | Hunt et al. |
| D595,620 S | 7/2009 | Kingsbury |
| D601,707 S | 10/2009 | Chouiller |
| 7,608,066 B2 | 10/2009 | Vogel |
| 7,618,382 B2 | 11/2009 | Vogel et al. |
| D608,006 S | 1/2010 | Avitable et al. |
| D612,947 S | 3/2010 | Turtzo et al. |
| D613,870 S | 4/2010 | Shust |
| 7,717,869 B2 | 5/2010 | Eischen, Sr. |
| D618,358 S | 6/2010 | Avitable et al. |
| D619,267 S | 7/2010 | Beckwith et al. |
| D620,122 S | 7/2010 | Cotton |
| 7,799,004 B2 | 9/2010 | Tumey |
| 7,804,686 B2 | 9/2010 | Parish et al. |
| D625,018 S | 10/2010 | Smith et al. |
| D626,241 S | 10/2010 | Sagnip et al. |
| D626,242 S | 10/2010 | Sagnip et al. |

(56) References Cited

U.S. PATENT DOCUMENTS

| | | |
|---|---|---|
| D626,243 S | 10/2010 | Sagnip et al. |
| D626,245 S | 10/2010 | Sagnip et al. |
| 7,811,269 B2 | 10/2010 | Boynton et al. |
| D627,896 S | 11/2010 | Matsuo et al. |
| D628,300 S | 11/2010 | Caden |
| 7,837,673 B2 | 11/2010 | Vogel |
| D630,759 S | 1/2011 | Matsuo et al. |
| 7,867,206 B2 | 1/2011 | Lockwood et al. |
| 7,871,387 B2 | 1/2011 | Tordella et al. |
| D631,971 S | 2/2011 | Turtzo et al. |
| D633,657 S | 3/2011 | Oban |
| D634,437 S | 3/2011 | Gramza et al. |
| D634,851 S | 3/2011 | Chiang |
| D635,266 S | 3/2011 | Chiang |
| D635,267 S | 3/2011 | Chiang |
| 7,896,910 B2 | 3/2011 | Schirrmacher et al. |
| 7,909,861 B2 | 3/2011 | Balachandran et al. |
| D636,497 S | 4/2011 | Giaccone |
| D638,950 S | 5/2011 | Janzon |
| D640,380 S | 6/2011 | Tweardy et al. |
| D640,381 S | 6/2011 | Tweardy et al. |
| 7,959,588 B1 | 6/2011 | Wolpa |
| 8,007,491 B2 | 8/2011 | Pinto et al. |
| D649,648 S | 11/2011 | Cavalieri et al. |
| 8,052,630 B2 | 11/2011 | Kloecker et al. |
| 8,084,663 B2 | 12/2011 | Watson, Jr. |
| 8,088,113 B2 | 1/2012 | Scherson et al. |
| 8,100,956 B2 | 1/2012 | Quisenberry et al. |
| 8,109,981 B2 | 2/2012 | Gertner et al. |
| D655,420 S | 3/2012 | Bowles |
| D655,821 S | 3/2012 | Matsuo |
| 8,128,672 B2 | 3/2012 | Quisenberry et al. |
| 8,142,486 B2 | 3/2012 | Quisenberry et al. |
| D657,063 S | 4/2012 | Chiang |
| 8,157,792 B2 | 4/2012 | Dolliver et al. |
| D660,438 S | 5/2012 | Kennedy et al. |
| D660,439 S | 5/2012 | Chen et al. |
| D662,212 S | 6/2012 | Quisenberry |
| D662,213 S | 6/2012 | Quisenberry |
| D662,214 S | 6/2012 | Quisenberry |
| 8,202,262 B2 | 6/2012 | Lina et al. |
| D663,850 S | 7/2012 | Joseph |
| D664,260 S | 7/2012 | Quisenberry |
| D665,088 S | 8/2012 | Joseph |
| D665,470 S | 8/2012 | Galbraith |
| D666,258 S | 8/2012 | Campbell |
| D666,301 S | 8/2012 | Joseph |
| 8,240,885 B2 | 8/2012 | Miller |
| 8,248,798 B2 | 8/2012 | Parish et al. |
| D679,023 S | 3/2013 | Quisenberry |
| 8,425,580 B2 | 4/2013 | Quisenberry et al. |
| D683,042 S | 5/2013 | Quisenberry |
| 8,444,581 B1 | 5/2013 | Maxon-Maldonado et al. |
| 8,449,483 B2 | 5/2013 | Eddy |
| 8,485,995 B1 | 7/2013 | Maxon-Maldonado |
| 8,529,613 B2 | 9/2013 | Radziunas et al. |
| 8,569,566 B2 | 10/2013 | Blott et al. |
| 8,574,278 B2 | 11/2013 | Quisenberry |
| 8,632,576 B2 | 1/2014 | Quisenberry |
| 8,753,300 B2 | 6/2014 | Deshpande |
| 8,753,383 B2 | 6/2014 | Parish et al. |
| 8,758,419 B1 | 6/2014 | Quisenberry et al. |
| 8,772,567 B2 | 7/2014 | Eckstein et al. |
| 8,778,005 B2 | 7/2014 | Parish et al. |
| 8,827,935 B2 | 9/2014 | Maxon-Maldonado |
| 8,834,393 B2 | 9/2014 | Maxon-Maldonado et al. |
| 8,940,034 B2 | 1/2015 | Quisenberry |
| 9,101,463 B2 | 8/2015 | Stormby |
| 9,114,055 B2 | 8/2015 | Edelman et al. |
| 9,119,705 B2 | 9/2015 | Parish et al. |
| 9,180,041 B2 | 11/2015 | Parish et al. |
| 9,192,539 B2 | 11/2015 | Parish et al. |
| 2001/0018604 A1 | 8/2001 | Elkins |
| 2001/0039439 A1 | 11/2001 | Elkins et al. |
| 2002/0116041 A1 | 8/2002 | Daoud |
| 2002/0143373 A1 | 10/2002 | Courtnage et al. |
| 2003/0050594 A1 | 3/2003 | Zamierowski |
| 2003/0083610 A1 | 5/2003 | McGrath et al. |
| 2003/0089486 A1 | 5/2003 | Parish et al. |
| 2003/0089487 A1 | 5/2003 | Parish, IV et al. |
| 2003/0127215 A1 | 7/2003 | Parish, IV et al. |
| 2003/0135252 A1 | 7/2003 | MacHold et al. |
| 2003/0139255 A1 | 7/2003 | Lina |
| 2003/0163183 A1 | 8/2003 | Carson |
| 2003/0171703 A1 | 9/2003 | Grim et al. |
| 2003/0176822 A1 | 9/2003 | Morgenlander |
| 2003/0191437 A1 | 10/2003 | Knighton et al. |
| 2004/0008483 A1 | 1/2004 | Cheon |
| 2004/0030281 A1 | 2/2004 | Goble et al. |
| 2004/0046108 A1 | 3/2004 | Spector |
| 2004/0054307 A1 | 3/2004 | Mason et al. |
| 2004/0068309 A1 | 4/2004 | Edelman |
| 2004/0068310 A1 | 4/2004 | Edelman |
| 2004/0099407 A1 | 5/2004 | Parish, IV et al. |
| 2004/0133135 A1 | 7/2004 | Diana |
| 2004/0176805 A1* | 9/2004 | Whelan .................... A61N 2/02 607/2 |
| 2004/0186535 A1* | 9/2004 | Knowlton ............... A45D 44/22 607/88 |
| 2004/0193218 A1 | 9/2004 | Butler |
| 2004/0210176 A1 | 10/2004 | Diana |
| 2004/0221604 A1 | 11/2004 | Ota et al. |
| 2004/0260231 A1 | 12/2004 | Goble et al. |
| 2005/0004636 A1 | 1/2005 | Noda et al. |
| 2005/0006061 A1 | 1/2005 | Quisenberry et al. |
| 2005/0033390 A1 | 2/2005 | McConnell |
| 2005/0039887 A1 | 2/2005 | Parish, IV et al. |
| 2005/0070828 A1 | 3/2005 | Hampson et al. |
| 2005/0070835 A1 | 3/2005 | Joshi |
| 2005/0080465 A1 | 4/2005 | Zelickson et al. |
| 2005/0126578 A1 | 6/2005 | Garrison et al. |
| 2005/0133214 A1 | 6/2005 | Pfahnl |
| 2005/0143797 A1 | 6/2005 | Parish et al. |
| 2005/0177093 A1 | 8/2005 | Barry et al. |
| 2005/0182364 A1 | 8/2005 | Burchman |
| 2005/0187500 A1 | 8/2005 | Perry et al. |
| 2005/0256556 A1 | 11/2005 | Schirrmacher et al. |
| 2005/0274120 A1 | 12/2005 | Quisenberry et al. |
| 2005/0284615 A1 | 12/2005 | Parish et al. |
| 2006/0034053 A1 | 2/2006 | Parish et al. |
| 2006/0058714 A1 | 3/2006 | Rhoades |
| 2006/0116620 A1 | 6/2006 | Oyaski |
| 2006/0167531 A1 | 7/2006 | Gertner et al. |
| 2006/0241549 A1 | 10/2006 | Sunnen |
| 2006/0253089 A1* | 11/2006 | Lin ....................... A61F 9/0026 604/301 |
| 2006/0276845 A1 | 12/2006 | George et al. |
| 2006/0282028 A1* | 12/2006 | Howard ............... A61M 27/00 602/2 |
| 2007/0032778 A1 | 2/2007 | Heaton et al. |
| 2007/0068651 A1 | 3/2007 | Gammons et al. |
| 2007/0112401 A1 | 5/2007 | Balachandran et al. |
| 2007/0118194 A1 | 5/2007 | Mason et al. |
| 2007/0129658 A1 | 6/2007 | Hampson et al. |
| 2007/0233209 A1 | 10/2007 | Whitehurst |
| 2007/0260162 A1 | 11/2007 | Meyer et al. |
| 2007/0282249 A1 | 12/2007 | Quisenberry et al. |
| 2008/0058911 A1 | 3/2008 | Parish et al. |
| 2008/0064992 A1 | 3/2008 | Stewart et al. |
| 2008/0071330 A1 | 3/2008 | Quisenberry et al. |
| 2008/0082029 A1 | 4/2008 | Diana |
| 2008/0103397 A1 | 5/2008 | Barak |
| 2008/0103422 A1 | 5/2008 | Perry et al. |
| 2008/0125775 A1* | 5/2008 | Morris ............... A61B 18/1477 606/50 |
| 2008/0132816 A1 | 6/2008 | Kane et al. |
| 2008/0132976 A1 | 6/2008 | Kane et al. |
| 2008/0249559 A1 | 10/2008 | Brown et al. |
| 2008/0262399 A1 | 10/2008 | Kovelman et al. |
| 2008/0319362 A1 | 12/2008 | Joseph |
| 2009/0069731 A1 | 3/2009 | Parish et al. |
| 2009/0109622 A1 | 4/2009 | Parish et al. |
| 2009/0149821 A1 | 6/2009 | Scherson et al. |
| 2009/0237264 A1 | 9/2009 | Bobey |

(56) References Cited

U.S. PATENT DOCUMENTS

| | | |
|---|---|---|
| 2009/0254159 A1 | 10/2009 | Stormby |
| 2009/0254160 A1 | 10/2009 | Shawver et al. |
| 2010/0010477 A1 | 1/2010 | Augustine et al. |
| 2010/0030306 A1 | 2/2010 | Edelman et al. |
| 2010/0081975 A1 | 4/2010 | Avitable et al. |
| 2010/0121230 A1 | 5/2010 | Vogel et al. |
| 2010/0137764 A1 | 6/2010 | Eddy |
| 2010/0145421 A1 | 6/2010 | Tomlinson et al. |
| 2010/0150991 A1 | 6/2010 | Bernstein |
| 2010/0179469 A1 | 7/2010 | Hammond et al. |
| 2010/0186436 A1 | 7/2010 | Stormby |
| 2010/0210982 A1 | 8/2010 | Balachandran et al. |
| 2010/0249679 A1 | 9/2010 | Perry et al. |
| 2010/0249680 A1 | 9/2010 | Davis |
| 2011/0009785 A1 | 1/2011 | Meyer et al. |
| 2011/0034861 A1 | 2/2011 | Schaefer |
| 2011/0037002 A1 | 2/2011 | Johnson et al. |
| 2011/0071447 A1 | 3/2011 | Liu et al. |
| 2011/0082401 A1 | 4/2011 | Iker et al. |
| 2011/0087142 A1 | 4/2011 | Ravikumar et al. |
| 2011/0275983 A1 | 11/2011 | Quisenberry et al. |
| 2011/0282269 A1 | 11/2011 | Quisenberry et al. |
| 2012/0041526 A1 | 2/2012 | Stormby |
| 2012/0259266 A1 | 10/2012 | Quisenberry |
| 2013/0030331 A1 | 1/2013 | Quisenberry et al. |
| 2013/0216627 A1 | 8/2013 | Galbraith et al. |
| 2013/0245508 A1 | 9/2013 | Maxon-Maldonado |
| 2013/0245519 A1 | 9/2013 | Edelman et al. |
| 2013/0253383 A1 | 9/2013 | Maxon-Maldonado |
| 2013/0261512 A1 | 10/2013 | Maxon-Maldonado et al. |
| 2013/0281947 A1 | 10/2013 | Quisenberry |
| 2013/0331767 A1 | 12/2013 | Quisenberry |
| 2014/0012169 A1 | 1/2014 | Wilford et al. |
| 2014/0046410 A1 | 2/2014 | Wyatt |
| 2014/0052054 A1 | 2/2014 | Quisenberry |
| 2014/0236271 A1 | 8/2014 | Fronda et al. |
| 2014/0257175 A1 | 9/2014 | Quisenberry |
| 2014/0316330 A1 | 10/2014 | Fudem et al. |
| 2014/0323949 A1 | 10/2014 | Quisenberry |
| 2015/0133849 A1 | 5/2015 | Quisenberry et al. |
| 2015/0290364 A1 | 10/2015 | Wall et al. |
| 2015/0328042 A1 | 11/2015 | Parish et al. |
| 2016/0030236 A1 | 2/2016 | Parish et al. |
| 2016/0067104 A1 | 3/2016 | Sarangapani et al. |
| 2016/0082238 A1 | 3/2016 | Wells et al. |
| 2016/0317348 A1 | 11/2016 | Banker |
| 2017/0119940 A1 | 5/2017 | Quisenberry |

FOREIGN PATENT DOCUMENTS

| | | | |
|---|---|---|---|
| EP | 0076074 A1 | 4/1983 | |
| EP | 0 489 326 | 6/1992 | |
| GB | 2373444 A | 9/2002 | |
| GB | WO 2005046760 A1 * | 5/2005 | .......... A61M 1/0058 |
| JP | 2009504246 A | 2/2009 | |
| SU | 689674 | 10/1979 | |
| WO | WO-1989009583 A2 | 10/1989 | |
| WO | WO-93/09727 | 5/1993 | |
| WO | WO-93/12708 A2 | 7/1993 | |
| WO | WO-9605873 A1 | 2/1996 | |
| WO | WO-9807397 A1 | 2/1998 | |
| WO | WO-1998016176 A1 | 4/1998 | |
| WO | WO-00/40186 | 7/2000 | |
| WO | WO-01/14012 A1 | 3/2001 | |
| WO | WO-01/54635 A1 | 8/2001 | |
| WO | WO-2004105676 A1 | 12/2004 | |
| WO | WO-2007019038 A2 | 2/2007 | |
| WO | WO-2008099017 A1 | 8/2008 | |
| WO | WO-2010124234 A1 | 10/2010 | |
| WO | WO-2012067918 A1 | 5/2012 | |

OTHER PUBLICATIONS

Young, Lee W., International Search Report of PCT Application No. PCT/US2014/64805, dated Mar. 13, 2015 (3 pages).
U.S. Appl. No. 12/730,060, Parish et al.
U.S. Appl. No. 12/708,422, Balachandran et al.
U.S. Appl. No. 12/871,188, Parish et al.
U.S. Appl. No. 13/107,264, Quisenberry.
U.S. Appl. No. 12/364,434, Quisenberry.
U.S. Appl. No. 13/190,564, Quisenberry et al.
U.S. Appl. No. 29/397,856, Quisenberry.
U.S. Appl. No. 29/400,194, Quisenberry.
U.S. Appl. No. 29/400,202, Quisenberry.
U.S. Appl. No. 29/400,212, Quisenberry.
U.S. Appl. No. 29/402,115, Quisenberry.
U.S. Appl. No. 13/796,139, Quisenberry.
U.S. Appl. No. 13/962,994, Quisenberry.
Artikis, T., PCT International Preliminary Report on Patentability as dated Jul. 29, 2005, (10 pgs.).
Tom Lee, T.Y. et al; "Compact Liquid Cooling System for Small, Moveable Electronic Equipment", IEEE Transactions on Components, Hybrids, and Manufacturing Technology, Oct. 15, 1992, vol. 15, No. 5, pp. 786-793.
Copenheaver, Blaine R., "International Search Report" for PCT/US2007/022148 dated Apr. 2, 2008, 2 pages.
Young, Lee W., "International Search Report" for PCT/US07/08807 dated Mar. 3, 2008, (3 pages).
Mahmoud Karimi Azar Daryany, et al., "Photoinactivation of *Escherichia coli* and *Saccharomyces cerevisiae* Suspended in Phosphate-Buffered Saline-A Using 266—and 355-nm Pulsed Ultraviolet Light", Curr Microbiol, vol. 56, 2008, pp. 423-428.
J. Li, et al.,"Enhanced germicidal effects of pulsed UV-LED irradiation on biofilms", Journal of Applied Microbiology, 2010, pp. 1-8.
Cyro/Temp Therapy Systems; Product News Catalogue; Jobst Institute, Inc., 6 pages (Copyright 1982).
Quisenberry, Tony, "U.S. Appl. No. 13/359,210" filed Jan. 26, 2012.
Quisenberry, Tony, "U.S. Appl. No. 29/424,860" filed Jun. 15, 2012.
Quisenberry, Tony, "U.S. Appl. No. 13/456,410" filed Apr. 26, 2012.
U.S. Appl. No. 15/227,417, filed Aug. 3, 2016, Overton et al.
U.S. Appl. No. 15/370,689, Quisenberry.
Hair Science Systems LLC, "Hair Science Systems—01 mobile unit—", Hair Saver Chemo Cold Cap, www.hairsciencesystems.com, 2 pages.
"U.S. FDA de novo clearance for the DigniCap® scalp cooling system that reduces hair loss related to chemotherapy for women with breast cancer", www.sysmex-europe.com/company/news-and-events/press-releases, accessed on Jun. 17, 2016, 3 pages.
"DigniLife—Prevention Of Chermotherapy-Induced Alopecia", www.sysmex.co.uk/products/oncology/scalp-cooling-system-dignilife, accessed on Jun. 17, 2016, 3 pages.

\* cited by examiner

WOUND CARE METHOD AND SYSTEM WITH ONE OR BOTH OF VACUUM-LIGHT THERAPY AND THERMALLY AUGMENTED OXYGENATION

CROSS-REFERENCE TO RELATED APPLICATIONS

This patent application continuation of U.S. patent application Ser. No. 13/359,210, filed Jan. 26, 2012. U.S. patent application Ser. No. 13/359,210 is a Continuation-in-Part of U.S. patent application Ser. No. 11/975,047 (now U.S. Pat. No. 8,128,672), filed on Oct. 17, 2007. U.S. patent application Ser. No. 13/359,210 claims priority from, and incorporates by reference the entire disclosure of, U.S. Provisional Patent Application No. 61/479,156, filed on Apr. 26, 2011. U.S. patent application Ser. No. 11/975,047 (now U.S. Pat. No. 8,128,672) is a Continuation-in-Part of U.S. patent application Ser. No. 11/801,662 (now U.S. Pat. No. 8,100,956), filed on May 9, 2007. U.S. patent application Ser. No. 11/975,047 claims priority to, and incorporates by reference the entire disclosure of, U.S. Provisional Patent Application No. 60/852,803, filed on Oct. 19, 2006. U.S. patent application Ser. No. 11/801,662 (now U.S. Pat. No. 8,100,956) claims priority to, and incorporates by reference the entire disclosure of, U.S. Provisional Patent Application No. 60/798,982, filed on May 9, 2006. This patent application incorporates by reference the entire disclosure of U.S. patent application Ser. Nos. 13/359,210; 11/975,047; and Ser. No. 11/801,662.

This patent application is related to and incorporates by reference U.S. Provisional Patent Application No. 60/488,709, filed on Jul. 18, 2003; U.S. Provisional Patent Application No. 60/550,658 filed on Mar. 5, 2004; and U.S. patent application Ser. No. 10/894,369, filed on Jul. 19, 2004. This patent application incorporates by reference commonly assigned U.S. Pat. Nos. 5,097,829; 5,989,285; and 6,935,409.

BACKGROUND OF THE INVENTION

Technical Field

The present invention relates to a wound care method and system with one or both of vacuum-light therapy, pulsed radio frequency ("RF"), and thermally augmented oxygenation, and more particularly, but not by way of limitation, to a programmable wound care control unit configured to generate a negative pressure for wound cleaning with light therapy, and, in one embodiment, pulsed RF or oxygenation of a wound area for healing in conjunction with high thermal contrast modalities generated by the control unit.

Description of the Related Art

An important aspect of patient treatment is wound care. Medical facilities are constantly in need of advanced technology for the cleaning and treatment of skin wounds. The larger the skin wound, the more serious the issues are of wound closure and infection prevention. The rapidity of the migration over the wound of epithelial and subcutaneous tissue adjacent the wound is thus critical. Devices have been developed and/or technically described which address certain aspects of such wound healing. For example, U.S. Pat. No. 6,695,823 to Lina et al. ("Lina") describes a wound therapy device that facilitates wound closure. A vacuum pump is taught for collecting fluids from the wound. WO 93/09727 discloses a solution for wound drainage by utilizing negative pressure over the wound to promote the above references migration of epithelial and subcutaneous tissue over the wound.

In other embodiments, wound treatment is performed using light therapy. For example, U.S. Pat. No. 7,081,128 to Hart et al. ("Hart") describes a method of treating various medical conditions such as, for example, joint inflammation, edema, etc., utilizing an array of Light Emitting Diodes contained on a flexible substrate that may be wrapped around an anatomical feature of the human body. U.S. Pat. No. 6,596,016 to Vreman et al. ("Vreman") discloses a phototherapy garment for an infant having a flexible backing material, a transparent liner, and a flexible printed circuit sheet containing surface-mounted LEDs. The LEDs preferably emit high-intensity blue light, suitable for the treatment of neonatal hyperbilirubinemia. The device may include a portable power supply.

In other embodiments, wound treatment is performed using oxygen. The use of oxygen for the treatment of skin wounds has been determined to be very beneficial in certain medical instances. The advantages are multitudinous and include rapidity in healing. For this reason, systems have been designed for supplying high concentration of oxygen to wound sites to facilitate the healing process. For example, U.S. Pat. No. 5,578,022 to Scherson et al. ("Scherson") teaches an oxygen producing bandage and method. One of the benefits cited in Scherson is the ability to modulate a supply of concentrated hyperbaric oxygen to skin wounds. Although oxygen is beneficial in direct application of predetermined dosages to skin wounds, too much oxygen can be problematic. Oxygen applied to a wound site can induce the growth of blood vessels for stimulating the growth of new skin. Too much oxygen, however, can lead to toxic effects and the cessation of healing of the wound. It would be an advantage, therefore, to maximize the effectiveness of oxygen applied to a wound area by enhancing the absorption rate of oxygen into the skin and tissue fluids. By enhancing the absorption rate of the oxygen in the wound, less exposure time and concomitantly fewer toxic side effects to the endothelial cells surrounding the wound, such as devasculation, occurs. It would be a further advantage, therefore, to utilize existing medical treatment modalities directed toward other aspects of patient therapy to augment oxygenation for wound care.

It has been accepted for many years by medical care providers that patient thermal therapy can be very advantageous for certain injuries and/or post operative recovery. For this reason, thermal therapy has been advanced and many reliable and efficient systems exist today which provide localized thermal therapy to patients in both pre and post surgical environments. In particular, absorption of oxygen by cells is enhanced by contrast thermal therapy wherein the wound area is heated prior to being saturated with oxygen and subsequently cooled.

Addressing first thermal therapy systems, several devices have been engineered to deliver temperature controlled fluids through pads or convective thermal blankets to achieve the above purpose. Typically, these devices have a heating or a cooling element, a source for the fluid, a pump for forcing the fluid through the pad or blanket, and a thermal interface between the patient and the temperature controlled fluid. U.S. Pat. No. 4,884,304 to Elkins ("Elkins") is, for example, directed to a mattress cover device which contains liquid flow channels which provide the selective heating or cooling by conduction.

Devices have also been developed for simply providing heat or cooling to a person in bed. Electric blankets containing electric heating elements have been used, for example, to provide heat to people in bed. Likewise, cooling blankets, such as the blanket disclosed in U.S. Pat. No. 4,660,388 to Greene ("Greene"), have also been proposed. Greene discloses a cooling cover having an inflatable pad with plenum chambers at opposite ends thereof. Cool air is generated in a separate unit and directed to the pad and out to a number of apertures on the underside of the pad and against the body of the person using the cover.

A disposable heating or cooling blanket is disclosed in U.S. Pat. No. 5,125,238 to Ragan et al. ("Ragan"), which has three layers of flexible sheeting. Two of the layers form an air chamber while a third layer includes a comfortable layer for contact with the patient. Conditioned air is directed toward the covered person through a multiplicity of orifices in the bottom layers of the blanket.

A temperature controlled blanket and bedding assembly is also disclosed in U.S. Pat. No. 5,989,285 to DeVilbiss et al. ("DeVilbiss"), assigned to the assignee of the present invention. DeVilbiss discloses a temperature controlled blanket and temperature control bedding system having the provision of both recirculating temperature controlled fluid and temperature controlled gas to enhance performance for convectively heating or cooling a patient. Counter-flow or co-flow heat exchanging principles between the temperature controlled liquid and the temperature controlled gas achieve temperature uniformity across different sections of the blanket and the bedding system. Drapes and the temperature controlled bedding system provide a temperature controlled envelope around a person using the bedding system. In one embodiment of the bedding system, the air portion of the bedding system is provided for use with a patient that supplies the fluid portion of the overall bedding system. In another embodiment of the bedding system, the fluid portion of the bedding system is provided for use with a patient bed which supplies the air portion of the overall bedding system.

U.S. Pat. No. 5,097,829 to Quisenberry ("Quisenberry") describes an improved temperature controlled fluid circulating system for automatically cooling a temperature controlled fluid in a thermal blanket with a thermoelectric cooling device having a cold side and a hot side when powered by electricity. The temperature controlled fluid is cooled by the cold side of the cooling device and pumped through, to, and from the blanket through first and second conduits.

Finally, co-pending U.S. patent application Ser. No. 10/894,369, assigned to the assignee of the present invention, teaches a sequential compression blanket for use with heating or cooling therapy. In this particular embodiment, the utilization of thermal therapy with sequential compression in a programmable format which further has the option of the introduction of oxygenation through a perforated membrane disposed between the patient and the thermal therapy pad is taught. These advances in the medical industry have been recognized as advantageous to both the medical care providers as well as the patients. The precise manner of oxygenation application is, however, still in the process of development.

The present invention provides improvements in wound care by providing multiple wound healing approaches such as, for example, the application of negative pressure over the wound area along with light therapy of the wound area, and oxygenation of the wound area in conjunction with thermal therapy. By combining an oxygenation modality that is utilized in conjunction with light and thermal therapy and/or sequential compression in association therewith, the individual benefits of negative wound pressure, light therapy, and oxygenation treatments can be synergistically enhanced.

SUMMARY

In one aspect, the present invention relates to a therapy system. The therapy system includes a therapy pad having a plurality of fiber-optic strands and a port. A pressure switch is fluidly coupled to the port. An oxygen source is fluidly coupled to the pressure switch. A vacuum pump is fluidly coupled to the pressure switch. A plurality of light emitting diodes is operationally coupled to the plurality of fiber-optic strands. The pressure switch adjusts the therapy pad between vacuum and oxygenation therapy.

In another aspect, the present invention relates to a therapy pad. The therapy pad includes an outer surface and an inner surface. A bladder is disposed between the outer surface and the inner surface. An array of fiber optic strands is disposed on the inner surface. An inlet is disposed on the outer surface. The inlet is fluidly coupled to a plurality of ports disposed on the inner surface. A radio frequency antenna is disposed on the inner surface.

In another aspect, the present invention relates to a method of treating a wound area. The method includes dressing the wound area with a therapy pad and administering at least one of ultra-violet light and vacuum therapy to the wound area via the therapy pad. In various embodiments, the method may also include administering oxygenation therapy to a wound area via the therapy pad, administering thermal therapy to the wound area via the therapy pad, and administering a pulsed radio frequency signal to the wound area via a radio frequency antenna disposed within the therapy pad.

BRIEF DESCRIPTION OF THE DRAWINGS

A more complete understanding of the method and apparatus of the present invention may be obtained by reference to the following Detailed Description when taken in conjunction with the accompanying Drawings wherein.

DETAILED DESCRIPTION

Various embodiments of the present invention will now be described more fully with reference to the accompanying drawings. The invention may, however, be embodied in many different forms and should not be construed as limited to the embodiments set forth herein; rather, the embodiments are provided so that this disclosure will be thorough and complete, and will fully convey the scope of the invention to those skilled in the art.

Figure 1:
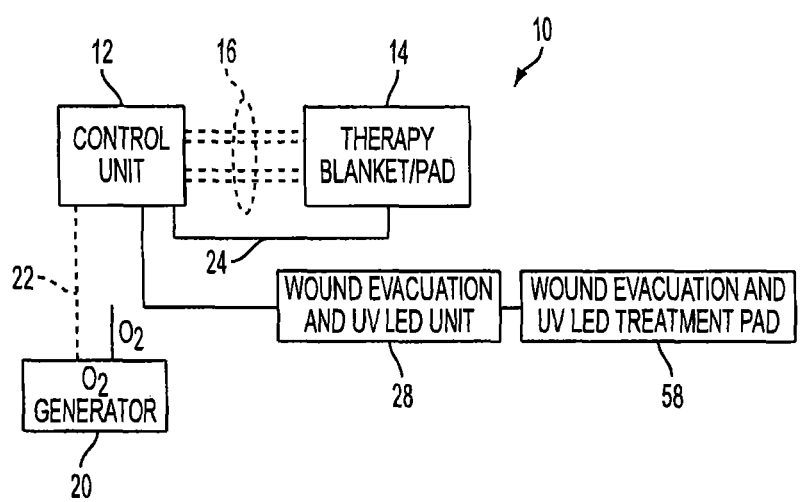
FIG. 1 is an illustration of the wound care system according to an exemplary embodiment.

Referring first to FIG. 1, there is shown an illustration of one embodiment of a wound care system 10 in accordance with principles of the present invention. The system 10 comprises a control unit 12, a therapy blanket/pad 14 and a plurality of tubular members 16 (to be defined below) connecting the control unit 12 to the therapy blanket/pad 14. The system 10 further includes a wound evacuation and ultra violet light emitting diode (UV LED) unit 28 and a wound evacuation and UV LED treatment pad 58. The wound evacuation and UV LED unit 28 is connected to the control unit 12 while the wound evacuation and UV LED treatment pad 58 is connected to the wound evacuation and UV LED unit 28. A system for providing both oxygenation therapy in conjunction with certain aspects of thermal therapy and fully describing the thermal operation and sequence compression aspects of one embodiment of the present invention is set forth and shown in U.S. patent application Ser. No. 10/894,369, assigned to the assignee of the present invention and incorporated herein in its entirety by reference. For that reason, thermal detail relative to the interaction between the control unit 12 and the therapy blanket/pad 14 relative to the thermal fluid flow and pressurization for sequenced compression therapy is not further defined herein. What is defined, is the added aspect of wound care provided by wound evacuation and light therapy. Light therapy is the application of light energy to the skin for therapeutic benefits. LED light therapy promotes wound healing and human tissue growth. Energy delivered by the LEDs enhances cellular metabolism, accelerates the repair and replenishment of damaged skin cells, as well as stimulates the production of collagen which is the foundation of a healthy and smooth skin. Light therapy is non-ablative, non-invasive, and painless.

Still referring to FIG. 1, the use of the therapy blanket/pad 14 to the wound site of the patient may be, in one embodiment, subsequent to the cleaning of the wound area of dead tissue by the wound evacuation and UV LED treatment pad 58. In one embodiment, Velcro cross straps may be utilized to secure the therapy blanket/pad 14. A 93% concentration of oxygen has been suggested to be advantageous when applied to a wound site as described herein with one or two atmospheres of pressure. In accordance with one aspect of the present invention, an oxygen generator/concentrator 20 may be utilized within the control unit 12 or may be separate therefrom. In FIG. 1, an oxygen generator/concentrator 20 is shown in association with the control unit 12 by dotted line 22 and an oxygenation gas line 24 shown extending between the control unit 12 and the therapy blanket/pad 14 as a diagrammatic illustration according to an embodiment of the present invention.

In FIG. 1, fiber optic strands (not explicitly shown) direct ultraviolet light from a plurality of LEDs (not explicitly shown) to an array of fiber optic strand ends (not explicitly shown) located on the undersurface of wound evacuation and UV LED treatment pad 58. The control unit 12 may be used to modulate the ultraviolet light to create various patterns of light, different intensities of light, and different durations of light. For example, the control unit 12 may be used to generate pulsed emission of ultraviolet light. The ultraviolet light is capable of penetrating through several layers of skin to destroy infectious bacteria. In one embodiment, not specifically shown herein, the UV LED treatment pad 58 may be provided on the therapy blanket/pad 14. According to exemplary embodiments, the ultraviolet light from the plurality of LEDs located on the undersurface of wound evacuation and UV LED treatment pad 58 destroys a wide variety of microorganisms such as, for example, bacteria which causes skin infections. In addition, the ultraviolet light from the plurality of LEDs improves wound healing along with cell and bone growth. Furthermore, the use of LEDs in light therapy is safe, non-invasive, drug-free and therapeutic.

Figure 2:
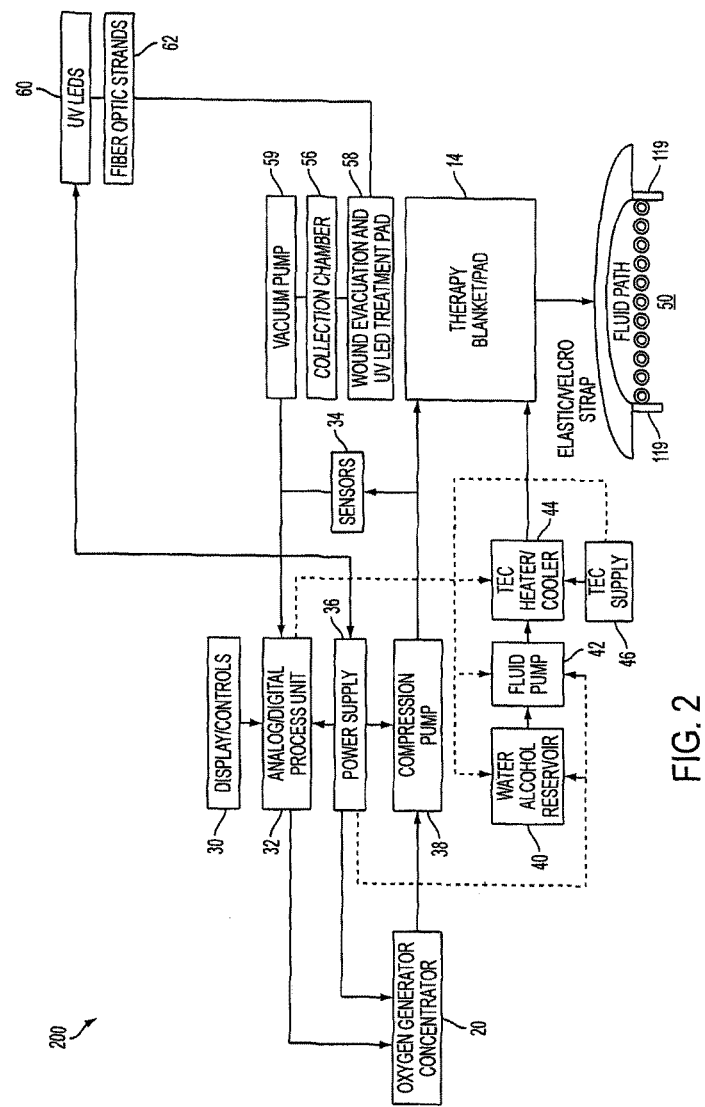
FIG. 2 is a block diagram according to an exemplary embodiment.

Referring now to FIG. 2, there is a block diagram 200 illustrating the flow of oxygenation gas as a transfer fluid according to an embodiment of the present invention. As set forth in the block diagram 200, a control unit display 30 is provided in conjunction with an analog/digital processing unit 32. A plurality of sensors 34 are utilized in conjunction with the processing unit 32 for control of heat transfer fluids to the therapy blanket/pad 14 as well as the oxygen delivery thereto. The oxygen generator/concentrator 20 is connected to a power supply 36, which power supply 36, also powers the processing unit 32. The oxygen generated from the oxygen generator/concentrator 20 is then pumped through compression pump 38 before delivery to the therapy blanket/pad 14. It should be noted that an oxygen supply may also be used.

Referring still to FIG. 2, a water/alcohol reservoir 40 is shown in fluid flow communication with fluid pump 42 and Thermo Electric Cooler (TEC) heater/cooler 44. The TEC heater/cooler 44 is controlled by the processing unit 32 and a TEC supply 46 is likewise shown. Adjacent the TEC supply 46 is illustrated a diagrammatical schematic of a treatment chamber 50 defined beneath the therapy blanket/pad 14 wherein the treatment chamber 50 is thermally exposed to the thermal fluid by the fluid path therein illustrated. The adhesive attachment edges 52 therein shown likewise define the treatment chamber space 50 between the therapy blanket/pad 14 and the wound site to allow for the flow of the oxygenation gas therein.

Referring still to FIG. 2, there is shown a vacuum pump 59 powered by the power supply 36. A collection chamber 56 is connected to the vacuum pump 59 and to a wound evacuation and UV LED treatment pad 58. The wound evacuation and UV LED treatment pad 58 is used prior to the therapy blanket/pad 14, in one embodiment of the present invention, for cleaning the wound area in preparation for oxygenation in conjunction with thermal therapy in accordance with the present invention.

Referring still to FIG. 2, there is shown a plurality of ultraviolet LEDs 60 and fiber optic strands 62, which are interoperably connected to the wound evacuation and UV LED treatment pad 58. The wound evacuation and UV LED treatment pad 58 is used prior to the therapy blanket/pad 14, in one embodiment of the present invention, for removing bacteria from the wound area in preparation for oxygenation in conjunction with thermal therapy in accordance with an embodiment. According to exemplary embodiments, ultraviolet light from the plurality of LEDs 60 destroys a wide variety of microorganisms such as, for example, bacteria which causes skin infections. In addition, the ultraviolet light from the plurality of LEDs 60 improves wound healing along with cell and bone growth. Furthermore, the use of the plurality of LEDs 60 in light therapy is safe, non-invasive, drug-free and therapeutic.

According to exemplary embodiments, the ultraviolet light from the plurality of LEDs 60 is in the range of approximately 200 to 450 nanometers and higher, and energy levels of up to 35,000 microwatt seconds/cm$^2$, which are necessary to eliminate or destroy most microorganisms such as bacteria, spores, algae and viruses. Most bacteria can be destroyed at ultra violet energies of from about 3,000 to about 5,000 microwatt-seconds/cm$^2$ while mold spores may require energies in the 20,000 to 35,000 mW-seconds/cm$^2$.

Figure 3:
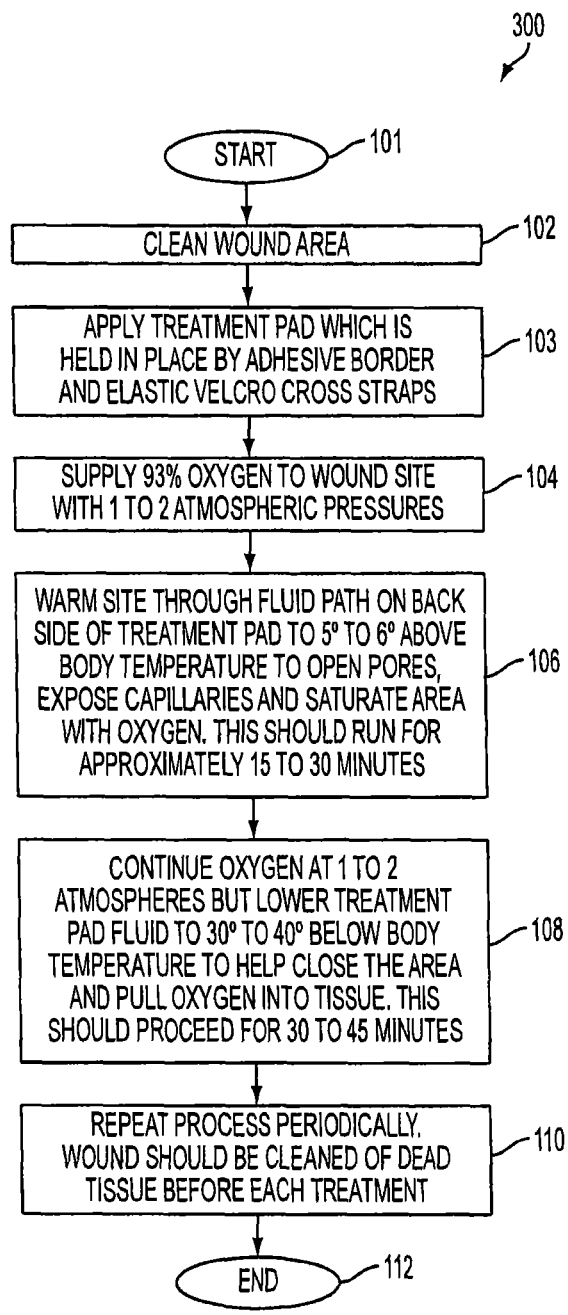
FIG. 3 is a flow diagram of a process according to an exemplary embodiment.

Referring now to FIG. 3 there is shown a flow diagram of a process 300 according to an embodiment. The process 300 starts at step 101. At step 102, the wound area is cleaned of dead tissue, any undesirable fluids, and bacteria by applying the wound evacuation and UV LED treatment pad 58. The wound evacuation and UV LED treatment pad 58 is used prior to the therapy blanket/pad 14 for removing bacteria from the wound area in preparation for oxygenation in conjunction with thermal therapy in accordance with the present invention. According to exemplary embodiments, the ultraviolet light from the plurality of LEDs located on the undersurface of wound evacuation and UV LED treatment pad 58 destroys a wide variety of microorganisms such as, for example, bacteria which causes skin infections. In addition, the ultraviolet light from the plurality of LEDs improves wound healing along with cell and bone growth. Furthermore, the use of LEDs in light therapy is safe, non-invasive, drug-free and therapeutic.

At step 103, the therapy blanket/pad 14 is applied to the wound area. The therapy blanket/pad 14 is held in position by an adhesive border and, in one embodiment, elastic Velcro cross straps. At step 104, according to an embodiment, an oxygenation gas comprising on the order of 93% concentration of oxygen gas is delivered to the wound site with one to two atmospheric pressures. The numbers as set forth and shown are exemplary and other oxygenation concentrations as well as pressures are contemplated in various embodiments. Consistent therewith, however, is the concept of, and teachings for, thermal treatment of the wound site in conjunction with oxygenation. In step 106, the site is warmed through the fluid path herein shown on the back side of the therapy blanket/pad 14 up to approximately 5 to approximately 6 degrees above the body temperature of the patient. Warming allows the pores of the patient's skin to open, exposing capillaries therein. The capillaries of the skin are then saturated with oxygen. In one period of time herein described, a warming period of approximately 15 to approximately 30 minutes is recommended. At step 108, oxygenation is continued at one to two atmospheres and the therapy blanket/pad fluid is lowered to approximately 30 to approximately 40 degrees below body temperatures. Cooling closes the pores of the wound area and pulls oxygen into the underlying tissue. Cooling then proceeds for approximately 30 to approximately 45 minutes in accordance with an embodiment. At step 110, the process 300 may be repeated periodically and the wound area may be cleaned of dead tissue before each treatment. At step 112, the process 300 ends.

Figure 4:
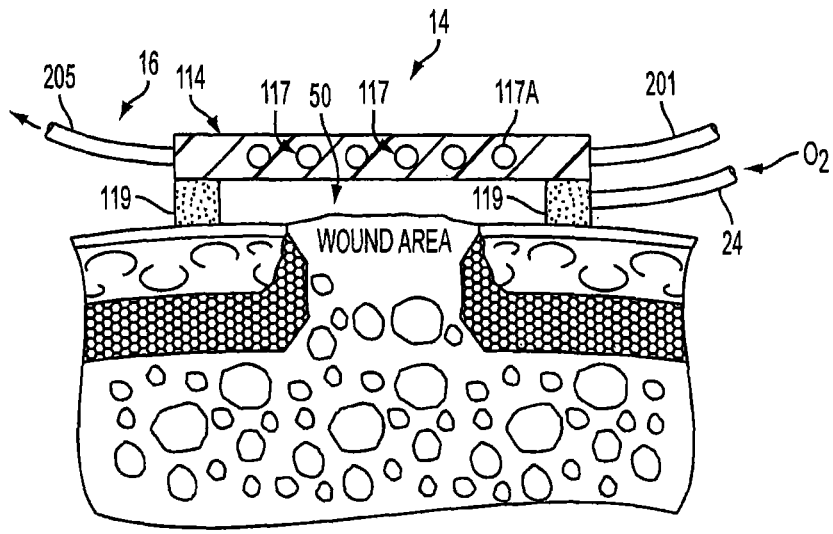
FIG. 4 illustrates a side elevational cross sectional view of a therapy blanket/pad according to an exemplary embodiment.

FIG. 4 is a side elevational, cross sectional view of one embodiment of the therapy blanket/pad 14. In an embodiment, the therapy blanket/pad 14 is constructed with a single bladder 114 where thermal fluid flow may be provided. The tubular members 16 are coupled to the therapy blanket/pad 14. The therapy blanket/pad is fabricated with a circuitous flow path therein for thermal fluid flow. The circuitous flow path may be tubular in form, or simply a path within therapy blanket/pad 14 defined by flow channels. What is shown is a path 117 within therapy blanket/pad 14. The path 117 is shown with tubular ends 117A, for example, illustrating that thermal fluid flows therein for thermal treatment of the underlying wound area. Again, the path 117 may not be of tubular form and may have a variety of shapes and fabrication techniques well know in the art of thermal pads.

According to an exemplary embodiment, the therapy blanket/pad 14 is separated from the patient's skin by adhesive strips 119 having a thickness of, for example, ⅛ inch. The therapy blanket/pad 14 (not drawn to scale) exposes the wound to both heat and cold via the path 117 while oxygen is injected into the treatment chamber 50. The injection of oxygen in conjunction with the aforesaid heating and cooling via the path 117 helps treat the wound area and any stasis zones therein where tissue swelling has restricted flow of blood to tissues within the wound area. It is well known that, without sufficient blood flow, the epithelial and subcutaneous tissues referenced above receive less oxygen and are less able to migrate over the wound area to promote healing. By utilizing the embodiments disclosed herein, oxygenation is enhanced and the problems associated with such conditions are mitigated.

Figure 5:
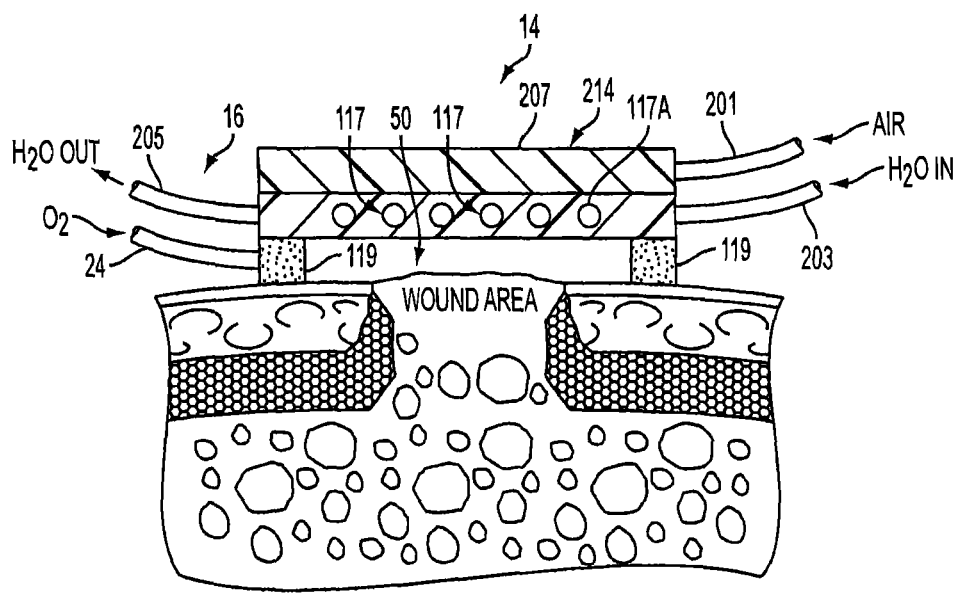
FIG. 5 illustrates a side elevational cross sectional view of a therapy blanket/pad according to an exemplary embodiment.

FIG. 5 illustrates an exemplary embodiment of the thermal therapy and oxygenation treatment pad of FIG. 4. A dual bladder 214 is thus provided where air may be applied to second bladder 207 atop the path 117, also represented by the "tubular" ends 117A shown for purposes of example only. In this manner, select compression therapy may be afforded in conjunction with the thermal and oxygenation treatment. In that regard, air inlet tube 201 is connected to the second bladder 207. Both FIGS. 4 and 5 show oxygen tube 24 for feeding oxygen to the treatment chamber 50, with tube 203 allowing thermal fluid into conduits 117 with tube 205 allowing thermal fluid return to control unit 12 of FIG. 1. FIG. 5 further illustrates the advantages of FIG. 4 with the ability for either compression or sequenced compression as referenced above.

Figure 6:
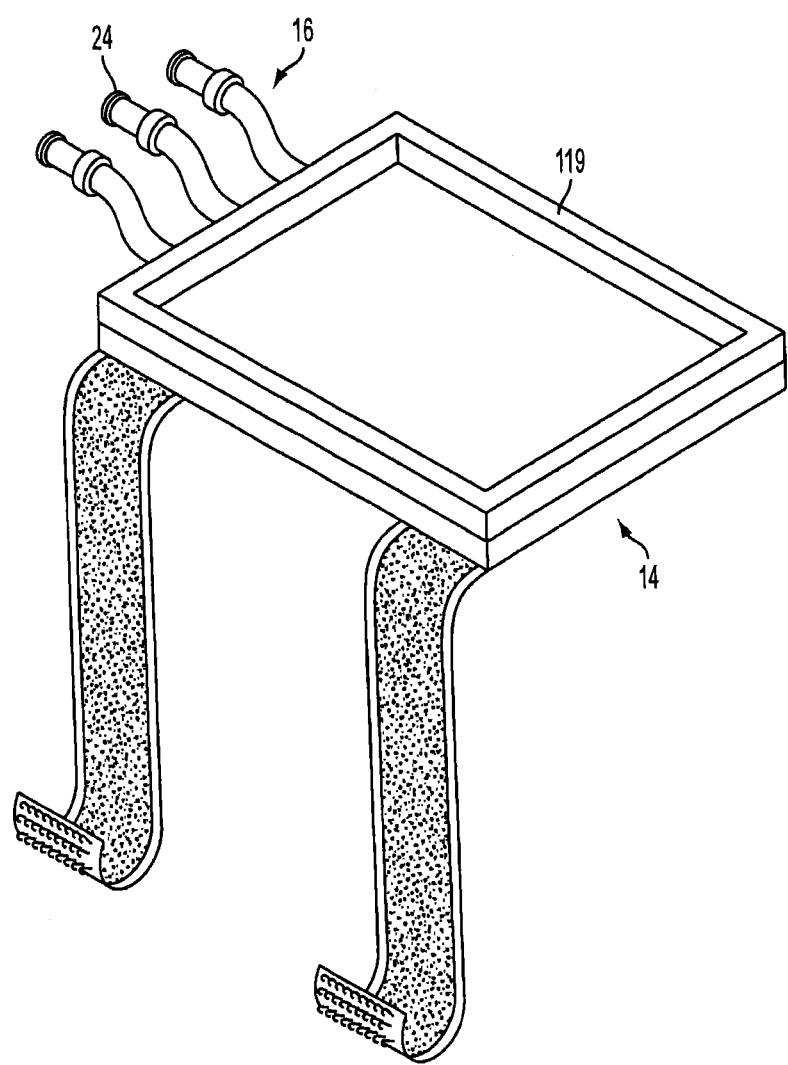
FIG. 6 is a diagrammatic illustration of a therapy blanket/pad according to an exemplary embodiment.

Referring now to FIG. 6, there is shown a diagrammatic illustration of the therapy blanket/pad 14 of FIGS. 1 and 4. The tubular members 16 for thermal fluid flow and the tube 24 for oxygen flow are clearly seen. The adhesive border 119 is likewise shown.

Figure 7:
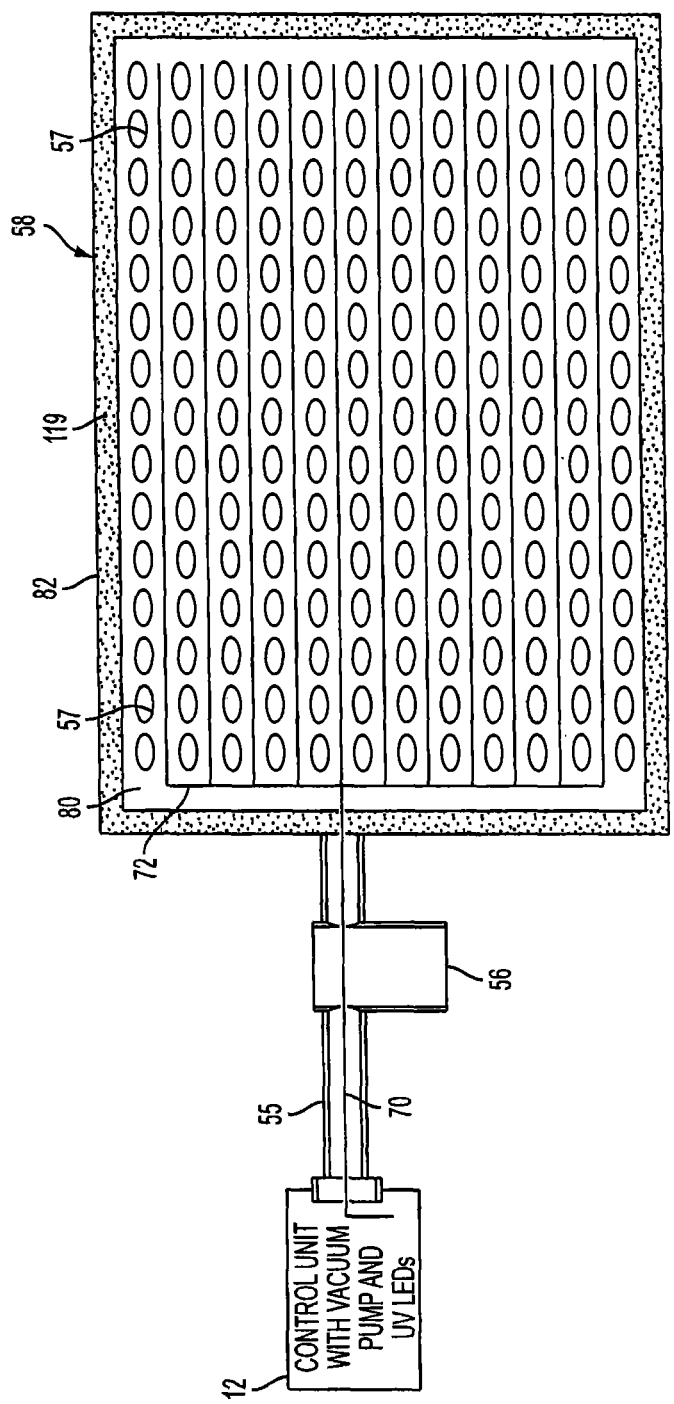
FIG. 7 is a diagrammatic illustration of a wound evacuation and UV LED treatment pad according to an exemplary embodiment.

FIG. 7 is diagrammatic illustration of a wound evacuation and UV LED treatment pad 58 according to an embodiment of the present invention. In this embodiment, the wound evacuation and UV LED treatment pad 58 contains an array of fiber optic strand 72 to project ultraviolet light onto a wound area (not explicitly shown). In a typical embodiment, the fiber optic strands 72 may be cleaved side emitting fibers. The wound evacuation and UV LED treatment pad 58 also contains an array of unique removal ports 57 that may be used to remove any undesirable fluid from the wound area. The wound evacuation and UV LED treatment pad 58 further contains a non-tissue adhesive service 80 which contains both the fiber optic strand array 72 and the unique removal ports 57. An adhesive circumference 82 is located around the periphery of the wound evacuation and UV LED treatment pad 58 to allow for a seal to be formed around the wound area. The seal, in conjunction with the removal ports 57, allows a negative pressure to form over the wound area. Negative pressure facilitates removal undesirable tissues from the wound area. The wound evacuation and UV LED treatment pad 58 is connected to a control unit 12. The control unit 12 contains a vacuum pump (not shown) and a plurality of ultraviolet LEDs (not explicitly shown). The vacuum pump is connected to the wound evacuation and UV LED treatment pad 58 via a vacuum line 55. A collection chamber 56 is positioned between the vacuum pump and the wound evacuation and UV LED treatment pad 58 to intercept and store undesirable fluids, tissues, and the like that are removed from the wound area as a result of negative pressure applied to the wound area with the vacuum pump. The plurality of ultraviolet LEDs transmit ultraviolet light through the fiber optic strands 70 to the wound evacuation and UV LED treatment pad 58, where the fiber optic strands 70 are then dispersed throughout the wound evacuation and UV LED treatment pad 58 to project ultraviolet light onto the wound area. Energy delivered by the plurality of LEDs enhances cellular metabolism, accelerates repair and replenishment of damaged skin cells, as well as stimulates production of collagen which is the foundation of a healthy and smooth skin. Light therapy is non-ablative, non-invasive, and painless.

Figure 8:
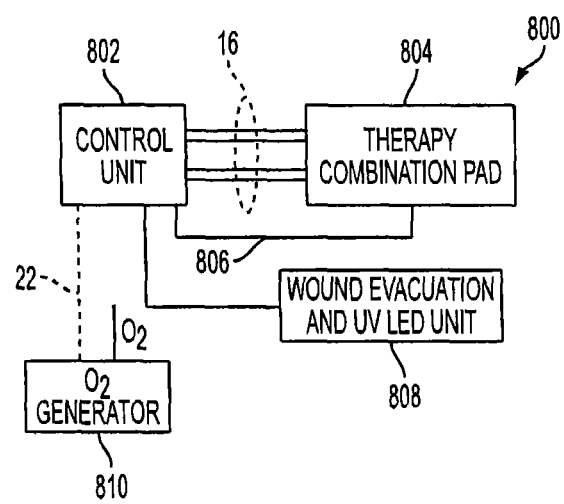
FIG. 8 is a schematic diagram of a wound care system according to an exemplary embodiment.

FIG. 8 is a schematic diagram of a wound care system according to an exemplary embodiment. In a typical embodiment, a wound care system 800 includes a control unit 802, a combination therapy pad 804, and a plurality of tubular members 806 connecting the combination therapy pad 804 to the control unit 802. In a typical embodiment, a wound evacuation and UV-LED unit 808 is associated with the control unit and connected to the combination therapy pad 804. In various embodiments, the wound evacuation and UV-LED unit 808 and the control unit 802 may be contained in a single housing; however, in various alternative embodiments, the wound evacuation and UV-LED unit 808 and the control unit 802 may be independent devices.

Still referring to FIG. 8, the use of the combination therapy pad 804 incorporates cleaning of a wound with ultraviolet light and evacuation with thermal and oxygenation therapy known to promote healing. In various embodiments, Velcro cross straps may be used to secure the combination therapy pad 804. In various embodiments, an oxygen generator/concentrator 810 may be utilized. The oxygen generator/concentrator 810 provides, for example, a 93% concentration of oxygen to a wound site. In a typical embodiment, the oxygen generator/concentrator 810 may be incorporated within the control unit 802; however, in other embodiments, the oxygen generator/concentrator 810 and the control unit 802 may be separate devices.

Still referring to FIG. 8, fiber optic strands (not explicitly shown) direct ultraviolet light from a plurality of LEDs (not explicitly shown) to an array of fiber optic strands (not explicitly shown) located on an undersurface of the combination therapy pad 804. The control unit 802 may be used to modulate the ultraviolet light to create, for example, various patterns of light, different intensities of light, and different durations of light. For example, in various embodiments, the control unit 802 can be used to produce pulsed emission of the ultraviolet light.

Figure 9:
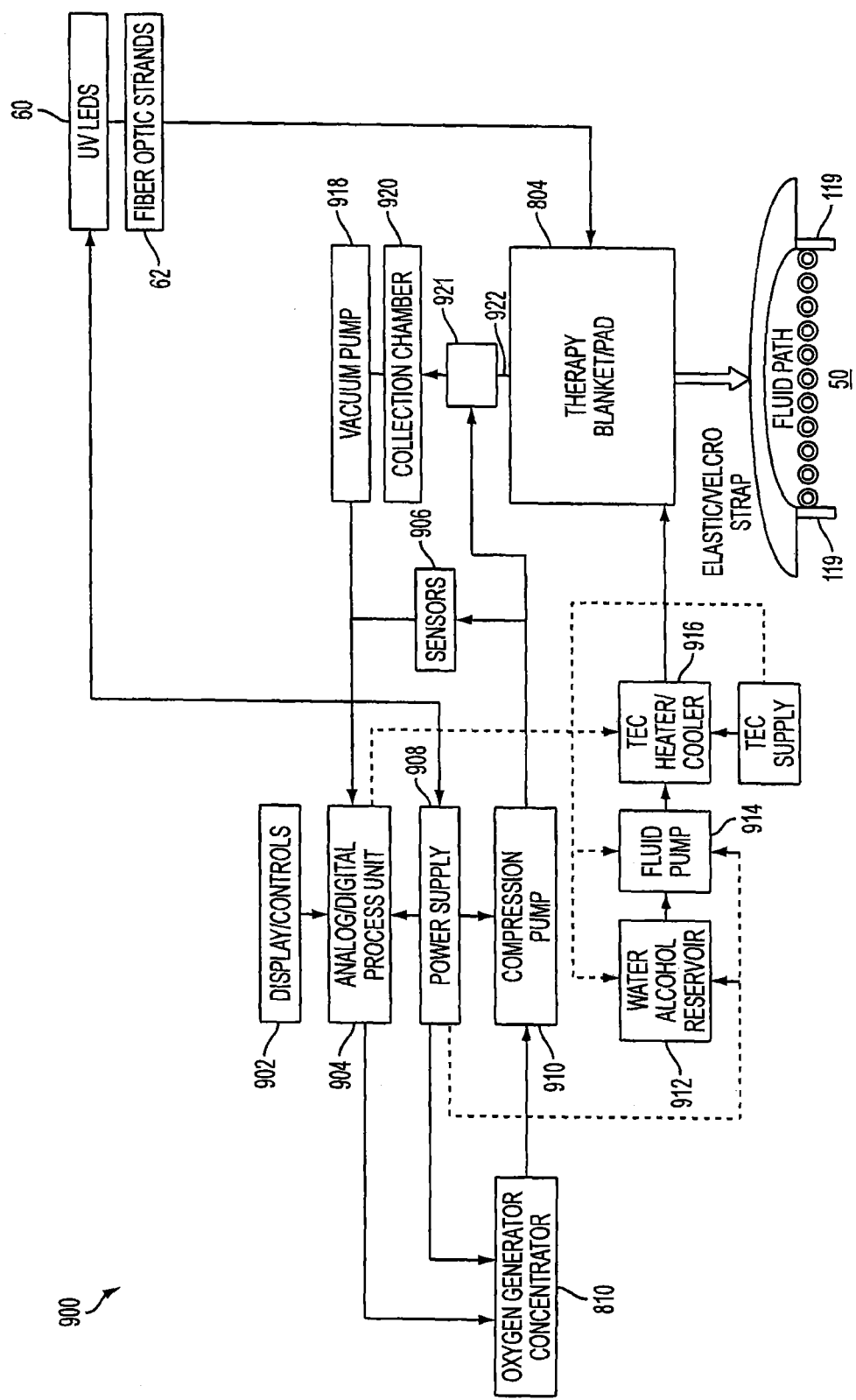
FIG. 9 is a is a block diagram of a wound care system according to an exemplary embodiment.

FIG. 9 is a block diagram of a wound care system according to an exemplary embodiment. In a wound-care system 900, a control unit display 902 is provided in conjunction with a processing unit 904. In a typical embodiment, the processing unit 904 is an analog/digital processing unit. A plurality of sensors 906 are utilized in conjunction with the processing unit 904 for control of heat transfer fluids to a combination therapy pad 804. In various embodiments, the oxygen generator/concentrator 810 is connected to a power supply 908. The power supply 908 also powers the processing unit 904. Oxygen generated by the oxygen generator/concentrator 810 is pumped through a compression pump 910 and a pressure switch 921 before being delivered to the combination therapy pad 804.

Still referring to FIG. 9, in a typical embodiment, a water/alcohol reservoir 912 is in fluid communication with a fluid pump 914 and a thermoelectric cooler 916. The thermoelectric cooler 916 is controlled by the processing unit 904. In a typical embodiment, a vacuum pump 918 is powered by the power supply 908. A collection chamber 920 is fluidly connected to the vacuum pump 918 and the pressure switch 921. The pressure switch 921 is fluidly coupled to the combination therapy pad 804. In a typical embodiment, oxygen therapy and vacuum therapy are each administered to the combination therapy pad 804 through a common port 922. In a typical embodiment, the pressure switch 921 is capable of adjusting the combination therapy pad 804 between vacuum treatment and oxygenation therapy.

Figure 10:
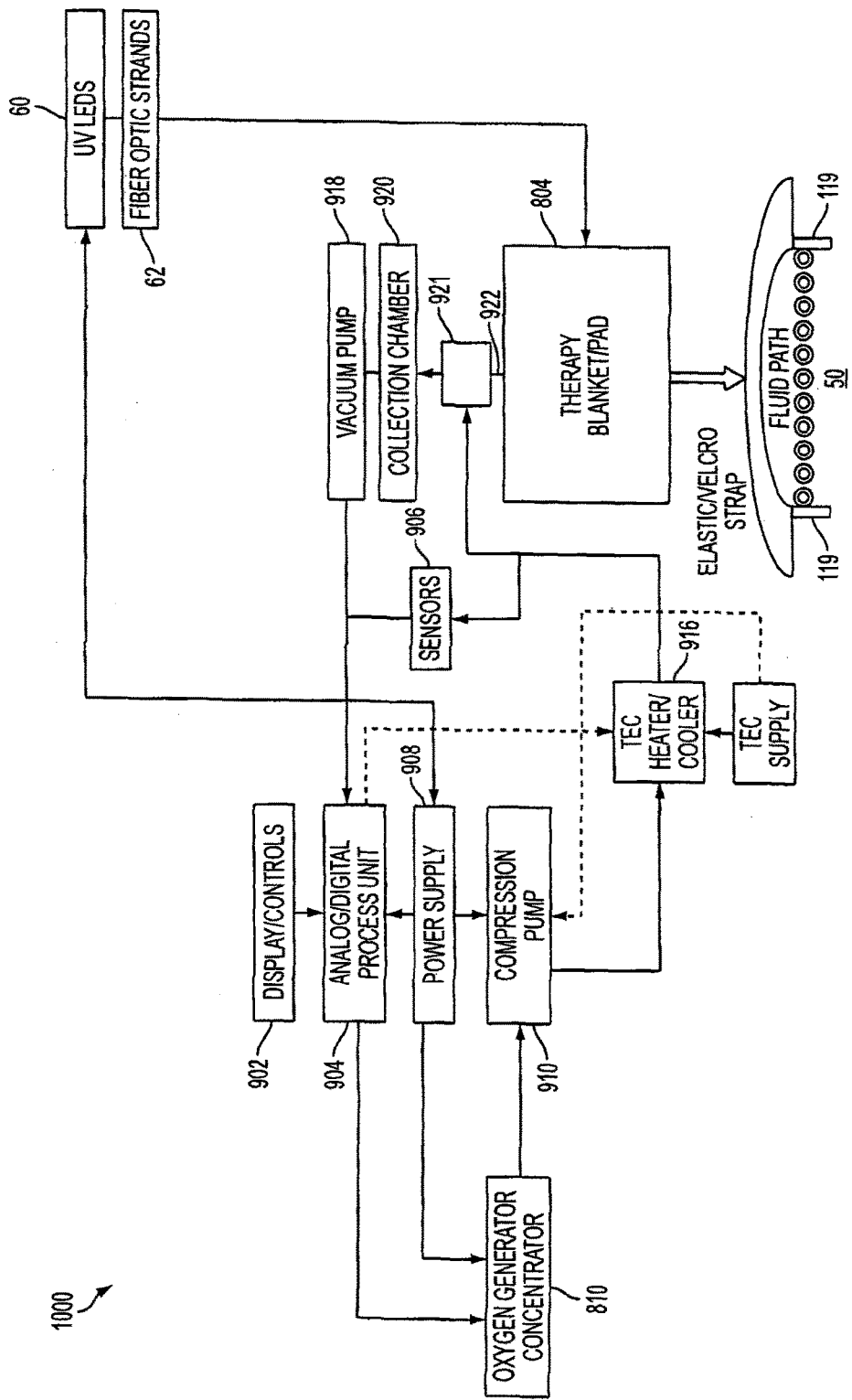
FIG. 10 is a block diagram of a wound care system according to an exemplary embodiment.

FIG. 10 is a block diagram of a wound care system according to an exemplary embodiment. In a typical embodiment, a wound care system 1000 is similar in construction to the arrangement described above with respect to FIG. 9. However, the wound care system 1000 does not include a water/alcohol reservoir or a fluid pump as shown in FIG. 9. In a typical embodiment, the thermoelectric cooler 916 is in fluid communication with the compression pump 910. Thus, thermal therapy is supplied to the combination therapy pad 804 through heating and cooling of the oxygen supplied by the oxygen generator/concentrator 810.

Figure 11:
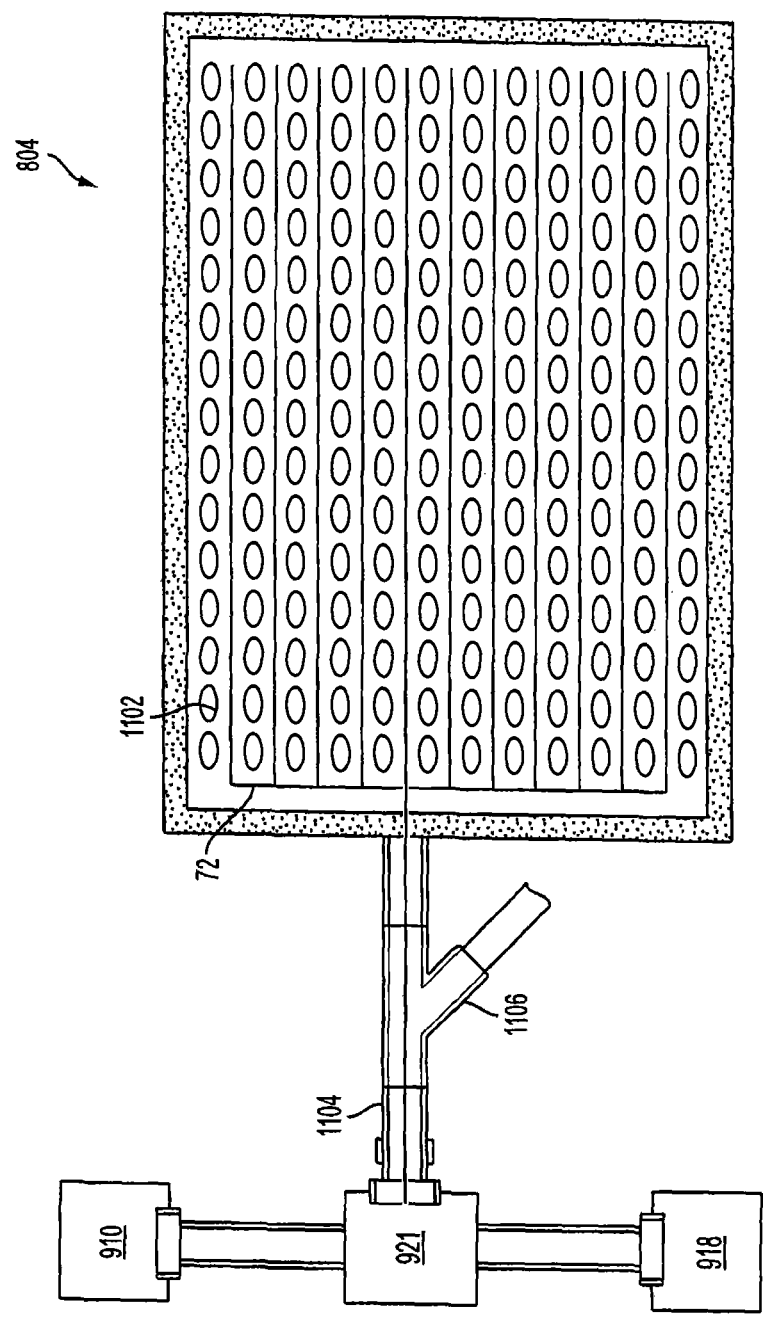
FIG. 11 is a diagrammatic illustration of a combination therapy pad according to an exemplary embodiment.

FIG. 11 is a diagrammatic illustration of a combination therapy pad according to an exemplary embodiment. In a typical embodiment, the combination therapy pad 804 includes a plurality of fiber optic strands 72 to project ultraviolet light onto a wound area (not explicitly shown). In various embodiments, the fiber optic strands 72 may be cleaved or side-emitting fibers; however, one skilled in the art will recognize that any type of fiber-optic strand could be used. In a typical embodiment, the combination therapy pad 804 also includes a plurality of oxygenation/removal ports 1102. In a typical embodiment, the oxygenation/removal ports 1102 alternate between providing oxygen therapy and vacuum therapy to the wound area.

Still referring to FIG. 11, in a typical embodiment, oxygen therapy and vacuum therapy is administered to the combination therapy pad 804 via an evacuation/oxygenation line 1104. The evacuation/oxygenation line 1104 is fluidly coupled to the pressure switch 921. The pressure switch 921 is fluidly connected to the compression pump 910 and the vacuum pump 918. Thus, in a typical embodiment, the pressure switch 921 is capable of adjusting the combination therapy pad 804 between vacuum treatment and oxygenation therapy.

Still referring to FIG. 11, in various embodiments, a luer lock 1106 is fluidly coupled to the combination therapy pad 804. During treatment, it is often necessary to administer various medications to a wound site. Such administration often requires removal of a wound dressing such as, for example, the combination therapy pad 804. Frequent removal of the wound dressing can increase risk of further damage to tissue immediately surrounding the wound site. In a typical embodiment, the luer lock 1106 allows for administration of medications and other therapeutic compounds directly to a wound site without the need to remove the combination therapy pad 804.

Figure 12:
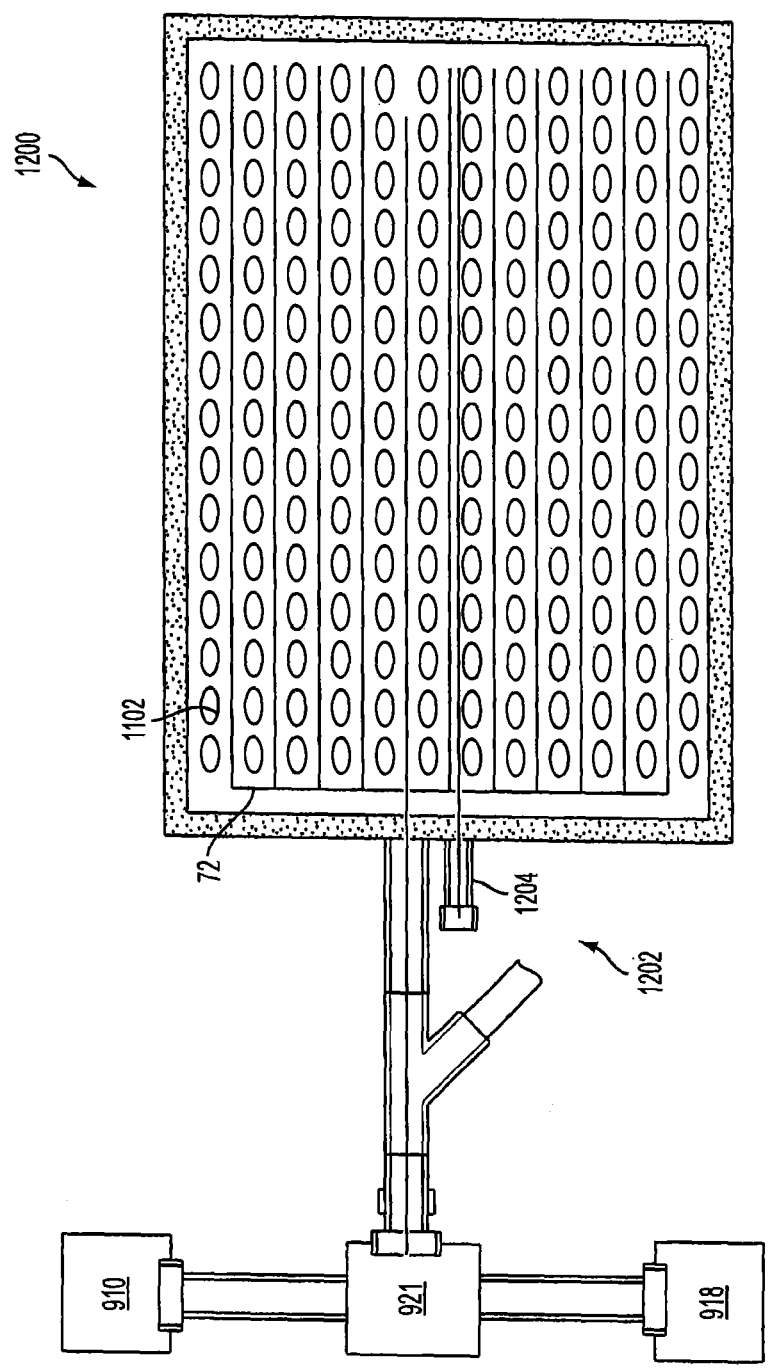
FIG. 12 is a diagrammatic illustration of a combination therapy pad according to an exemplary embodiment.

FIG. 12 is a diagrammatic illustration of a combination therapy pad according to an exemplary embodiment. In a typical embodiment, the combination therapy pad 1200 includes the plurality of fiber optic strands 72 to project ultraviolet light onto a wound area (not explicitly shown). In a typical embodiment, a combination therapy pad 1200 also includes a radio frequency ("RF") antenna 1202. In a typical embodiment, the RF antenna 1202 comprises a wire 1204. The wire 1204 extends along a length of the combination therapy pad 1204. In a typical embodiment, the wire 1204 is disposed within the combination therapy pad 1200 so that, during use, the wire is in close proximity to a wound area. In various embodiments, the wire 1204 is insulated to reduce risk of electric shock to a patient.

FIG. 13 is an exploded view of a combination therapy pad according to an exemplary embodiment. The combination therapy pad 1200 includes a first layer 1302 having a first central gap 1304 formed therein. In a typical embodiment, the first layer 1302 is constructed of, for example, urethane. A second layer 1305 is disposed below the first layer 1302. In a typical embodiment, the second layer 1305 is constructed of, for example, urethane and includes an adhesive bottom surface 1306. A second central gap (not explicitly shown) is formed in the second layer 1305. In a typical embodiment, the second central gap aligns with the first central gap 1304. A fiber-optic array 1308 is disposed between the first layer 1302 and the second layer 1305 so as to fill a space defined by the first central gap 1304 and the second central gap.

Still referring to FIG. 13, a third layer 1310 is disposed above the first layer 1302. The third layer 1310 includes a recessed central area 1312. The recessed central area 1312 is fluidly coupled to a vacuum tube 1314 and a therapeutic fluid tube 1316. An antenna 1318 is coupled to the third layer 1310. In a typical embodiment, the antenna 1318 is formed into a loop and is generally arranged around a perimeter of the recessed central area 1312. In a typical embodiment, the first layer 1302, the second layer 1305, and the third layer 1310 are coupled to each other via process such as, for example, adhesive bonding or welding.

Still referring to FIG. 13, during operation, the adhesive bottom surface 1306 is placed on a bodily region of a patient proximate a wound area. In a typical embodiment, the adhesive bottom surface 1306 is oriented such that the second central gap is positioned over the wound area. Thus, the adhesive bottom surface 1306 is not in direct contact with the wound area. The fiber-optic array 1308 is disposed over the wound area and, in various embodiments, may contact the wound area.

Still referring to FIG. 12, during operation, a pulsed radio-frequency ("RF") signal having a pulse frequency on the order of, for example 27 MHz, is transmitted to the wire 1204. In a typical embodiment, an amplitude of the pulsed RF signal is on the order of, for example, a fraction of a Watt. Such an amplitude is below a threshold where federal licensing is typically required. The wire 1204 receives the pulsed RF signal and transmits the pulsed RF signal to a region in close proximity to the wound area. Exposing the wound area to the pulsed RF signal has been shown to be beneficial to healing by encouraging intracellular communication. In particular, pulsed RF signals have been shown to stimulate cellular bonding, and metabolism.

The previous Detailed Description is of embodiment(s) of the invention. The scope of the invention should not necessarily be limited by this Description. The scope of the invention is instead defined by the following claims and the equivalents thereof.

What is claimed is:

1. A therapy pad comprising:
   a thermal fluid flow path disposed within the therapy pad;
   an array of fiber optic strands disposed on the therapy pad and positioned on a side facing a wound when the pad is placed thereover to project ultraviolet light onto the wound;
   an adhesive strip disposed on the therapy pad, the adhesive strip separating the therapy pad from the wound when the pad is placed thereover;
   the thermal fluid flow path comprising an inlet fluidly coupled to a vacuum pump and an oxygen concentrator, the inlet defining a flow path to a plurality of ports formed on the side of the therapy pad facing the wound, the inlet and the plurality of ports being adapted to provide at least one of oxygenation and vacuum therapy to the wound; and
   a radio frequency antenna comprising a wire that extends along a length of the therapy pad on a surface of the therapy pad facing the wound.

2. The therapy pad of claim 1, wherein the radio frequency antenna receives a pulsed radio-frequency signal.

3. The therapy pad of claim 2, the pulsed radio frequency signal is approximately 27 MHz.

4. The therapy pad of claim 2, wherein the pulsed radio frequency signal stimulates cellular bonding thereby promoting healing of a wound area.

5. The therapy pad of claim 1, further comprising a luer lock fluidly coupled to the inlet.

6. A method of treating a wound area, the method comprising:
   dressing the wound area with a therapy pad;
   administering ultra-violet light to the wound area via the therapy pad;
   administering, via the therapy pad at least one of vacuum therapy and oxygenation therapy to wound area;
   administering, via the therapy pad, thermal therapy to the wound area; and
   administering a pulsed radio frequency signal to the wound area via a radio frequency antenna disposed within the therapy pad.

7. The method of claim 6, wherein the administering thermal therapy comprises circulating a heat transfer fluid through the therapy pad.

8. The method of claim 6, wherein the administering thermal therapy comprises providing at least one of heated and cooled oxygen to the wound area via the therapy pad.

9. The method of claim 6, wherein the administering the pulsed radio frequency signal comprises administering a signal of approximately 27 MHz.

10. The method of claim 6, further comprising administering a medication to the wound area via a luer lock disposed with the therapy pad.

* * * * *